United States Patent [19]

Fleche

[11] Patent Number: 5,731,467
[45] Date of Patent: Mar. 24, 1998

[54] PROCESS FOR THE MANUFACTURE OF XYLARIC ACID AND USES THEREOF

[75] Inventor: Guy Fleche, Hazebrouck, France

[73] Assignee: Roquette Freres, Lestrem, France

[21] Appl. No.: 677,307

[22] Filed: Jul. 9, 1996

[30] Foreign Application Priority Data

Jul. 11, 1995 [FR] France .................. 95 08363

[51] Int. Cl.⁶ .................................. C07C 51/16
[52] U.S. Cl. ................ 562/525; 562/523; 562/580; 562/582; 562/587; 562/590; 562/593
[58] Field of Search ................ 562/525, 523, 562/580, 582, 587, 590, 593

[56] References Cited

U.S. PATENT DOCUMENTS

| | | | |
|---|---|---|---|
| 2,318,641 | 5/1943 | Stubbs et al. | 435/137 |
| 2,338,114 | 1/1944 | Isbell | 260/535 |
| 2,587,906 | 3/1952 | Schmidt | 260/528 |
| 2,614,122 | 10/1952 | Mikeska et al. | 562/525 |
| 2,847,466 | 8/1958 | Steadman et al. | 562/525 |
| 4,125,559 | 11/1978 | Scholz et al. | 562/531 |
| 4,833,230 | 5/1989 | Kiely et al. | 528/230 |

FOREIGN PATENT DOCUMENTS

| | | |
|---|---|---|
| 620 248 | 9/1935 | Germany . |
| 190540 | 7/1937 | Switzerland . |
| WO 93/19030 | 9/1993 | WIPO . |
| Wo 94/04650 | 3/1994 | WIPO . |

OTHER PUBLICATIONS

J. Org. Chem. vol. 42, No. 22, 1977 pp. 3562–3567 Cantrell, Kiely, Abruscato and Riordan No Month Provided.
Journal of Molecular Catalysis, 77 (1992) 75–85 Fokko R. Venema et al. No Month Provided.
Carbohydrate Research, 214 (1991) 71–85 Henricus E. J. Hendriks et al. No Month Provided.

*Primary Examiner*—Gary Geist
*Assistant Examiner*—Rosalynd A. Keys
*Attorney, Agent, or Firm*—Henderson & Sturm

[57] ABSTRACT

Process for the manufacture of xylaric acid, characterized in that it consists of the oxidative degradation of 5-ketogluconic acid in alkaline medium using oxygen or a gas containing it.

The xylaric acid obtained is of use as a calcium-chelating agent or as a component of polyhydroxypolyamides or as an intermediate in the synthesis of xylitol.

14 Claims, No Drawings

PROCESS FOR THE MANUFACTURE OF XYLARIC ACID AND USES THEREOF

The present invention relates to a process for the manufacture of xylaric acid.

More precisely, the invention relates to a process for the manufacture of xylaric acid by alkaline oxidative degradation of 5-ketogluconic acid.

Xylaric acid, of empirical formula $HOOC-(CHOH)_3-COOH$, is a trihydroxydicarboxylic acid belonging to the class of trihydroxyglutaric acids whose uses could be numerous if it became possible to produce it in large quantities.

As a polyhydroxycarboxylic acid it has, like most of the acids of this class, complexing properties which could afford it a place of choice in the formulation of phosphate-free detergent compositions. In this respect, worldwide patent application WO 94/04650 claims, for this type of detergent composition, the use of polyhydroxydicarboxylic acids having from 4 to 6 carbon atoms and at least two hydroxyl functions per molecule. Tartaric acids (4 carbon atoms and 2 hydroxyl functions) and galactaric and glucaric acids (6 carbon atoms and 4 hydroxyl functions) are mentioned among the acids which satisfy these conditions.

As a dicarboxylic acid, bearing acidic functions at the ends of a linear carbon chain, xylaric acid may enter into the composition of polymers of the polyhydroxypolyamide type. These polymers consist of regularly alternating units: an aldaric acid unit and a unit of a primary diamine. They find applications in the fields of textiles, security glasses, adhesives, aqueous emulsions of paint, fibres, plastics and liquid crystals. In this respect, American patent U.S. Pat. No. 4,833,230 describes polyhydroxypolyamides obtained from glucaric acid, galactaric acid and xylaric acid.

As a trihydroxydicarboxylic acid, xylaric acid may be reduced, for example using metal hydrides or by catalytic hydrogenation, to the corresponding pentitol which is xylitol. Xylitol is a polyalcohol which is of great value as a sweetener.

Xylitol is a naturally existing product which is almost as sweet as sugar, but which possesses over sugar the advantage of not causing dental caries.

However, the processes developed to date to obtain xylaric acid are not satisfactory. These processes for the production of xylaric acid, and more generally of an aldaric acid, consist mainly in oxidizing the corresponding aldose with nitric acid (C. E. Cantrell et al. J. Org. Chem., 42, 3562 (1977)), or, less frequently, in oxidizing this aldose using oxygen and a metal catalyst (F. R. Venema et al., J. of Molecular Catalysis, 77 (1992) 75–85). However, these processes give poor yields. In the case of the oxidation of xylose with nitric acid, less than 45% xylaric acid is obtained and it is necessary to use expensive organic solvents. Using platinum-alumina-based catalysts the conversion, without recovery of the crystallized product, does not exceed 58%. Above all, however, these oxidation processes suffer from the drawback of using xylose as starting material for the manufacture of xylaric acid. The basis of the drawback is that xylose is a pentose which is difficult to obtain, being liberated only in small amounts by hydrolysis, under drastic conditions, of hemicellulosic starting materials such as wood, straw and corn cobs.

None of these processes used to obtain xylaric acid has to date proven to be economic or efficient, thus confining this product to advantageous potentials in a role more similar to laboratory curiosities than to those potentials it might have as an industrial product or as a major synthetic intermediate.

There was thus a need to develop a high-performance process for the production of xylaric acid from abundant and inexpensive starting materials, and, after having identified this need, this is what the Applicant has managed to achieve.

The main subject of the present invention is thus a process for the manufacture of xylaric acid which consists of the oxidative degradation of 5-ketogluconic acid in alkaline medium using oxygen or a gas containing it.

The subject of the invention is also the use of the xylaric acid obtained by the process of the invention as an intermediate in the synthesis of xylitol, its use as a component of polyhydroxypolyamides or its use as a calcium-chelating agent in particular in washing formulations.

More precisely, the process for the manufacture of xylaric acid according to the invention is based on the fact that the Applicant has discovered that the process of Spengler and Pfannenstiel (German patent No. 620,248) could be applied successfully using 5-ketogluconic acid to give xylaric acid.

These inventors had observed that finely divided air in an alkaline solution of an aldose or of a ketose degraded the latter, in good yield, to the corresponding aldonic acid of immediately lower rank, on the one hand, and to formic acid, on the other hand.

When performed on glucose, mannose or fructose, this alkaline oxidative degradation is reflected especially by the production of arabinoic and formic acids, and when carried out on sorbose, as indicated for example in patent application PCT 93/19030, it leads especially to the production of xylonic and formic acids.

Various improvements have been made to the Spengler and Pfannenstiel process, for example H. E. J. Hendriks et al., Carbohydrate Research, 214 (1991) 71–85 proposed, in order to increase the yields and the specificity of the reaction for the oxidation of reducing sugars, to use, as an oxidative degradation catalyst, anthraquinone 2-sulphonate activated by hydrogen peroxide and to carry out the reaction with pure oxygen. American patent U.S. Pat. No. 2,587,906 recommended using catalysts consisting of methylene blue and analogues thereof from the thiazine, oxazine and phenazine series in order to oxidize reducing sugars. American patent U.S. Pat. No. 4,125,559 recommended especially, for the same purpose, working with pure oxygen at pressures which may be up to 40 bar.

However, to the Applicant's knowledge, this type of alkaline oxidative degradation has never been used on 5-ketogluconic acid, which, correctly speaking, is neither an aldose nor a ketose.

The subject of the present invention is thus also a process for the manufacture of xylaric acid which consists of the oxidative degradation of 5-ketogluconic acid in alkaline medium using oxygen or a gas containing it, characterized in that the oxidative degradation is carried out in the presence of catalysts and/or under pressure.

Although 5-ketogluconic acid has already been proposed as a starting material for the synthesis of tartaric acid, vitamin C, 5-carboxy-D-gluconate or 5-amino derivatives of gluconic acid, it has, however, to the Applicant's knowledge, never been proposed in order to obtain xylaric acid nor, all the less, as an intermediate in the synthesis of xylitol. In the same manner, it does not appear that xylaric acid has already been proposed specifically as a good calcium-chelating agent.

5-Ketogluconic acid, the production of which was first described by Boutroux as early as 1880, is very readily obtained from glucose by aerobic fermentation of this glucose using various strains of acetobacter or of gluconobacter, in a medium containing nutrients supplied, for example, by a corn steep liquor. Such a fermentation is described in particular in American patent U.S. Pat. No. 2.318.641.

The recovery and purification of calcium 5-ketogluconate at the end of the fermentation is greatly facilitated by the fact that this calcium salt of 5-ketogluconic acid, obtained in the form Ca $(C_6H_8O_7)_2.2.5H_2O$ is very sparingly soluble in water (about 2 g/l at 20° C.) and that it may thus readily be freed of its main contaminants, namely calcium 2-ketogluconate and unfermented glucose, by simple filtration.

The free acid may readily be regenerated from its purified calcium salt by precipitation of calcium sulphate or calcium oxalate using sulphuric acid or oxalic acid, or converted into another soluble salt of sodium or of potassium by subsequent neutralization with a suitable base.

In order to obtain xylaric acid according to the process of the invention, the process may be performed as follows or in an equivalent manner:

A 5-ketogluconic acid salt is placed in solution or in suspension in water at a concentration preferably of between 50 and 500 g/l, in a reactor provided with stirring and aeration means, as well as a temperature-control system. A base generally corresponding to the acid salt used is then added to this solution or suspension, in an amount such that it is able to form an alkaline reserve which is sufficient to maintain a pH of above 12.5 to the end of the alkaline oxidative degradation.

This base may also be introduced progressively into the reaction medium as the oxidative degradation reaction proceeds, taking care to maintain the pH of the reaction medium at a value of above 12.5.

Conversely, it is also possible to prepare a solution of the base and to introduce the 5-ketogluconic acid salt progressively therein.

In order for the process to be efficient and for good yields to be obtained, it is generally preferable, as Spengler and Pfannenstiel have demonstrated, for the alkaline oxidative degradation reaction to take place in the presence of air which is very finely divided in the medium. The air may, obviously, be enriched with oxygen or replaced by oxygen. Similarly, it is possible to work at pressures above atmospheric pressure, and this reaction may also be carried out in the presence of catalysts. This allows the selectivity and yield of this reaction to be increased. In general, sufficiently finely divided gas bubbles are obtained by stirring the reaction medium vigorously using propellers or turbomixers.

The reaction for the oxidative alkaline degradation of 5-ketogluconic acid, which is essentially reflected by the formation of one mole of xylaric acid and one mole of formic acid per mole of 5-ketogluconic acid used, is preferably carried out by maintaining the temperature of the reaction medium between 20° and 60° C. However, it is preferred to work with this temperature being maintained between 40° and 50° C.

When this oxidative alkaline degradation is carried out in the presence of a catalyst, an equimolar mixture of anthraquinone 2-sulphonate and hydrogen peroxide is preferably used, in an amount generally of between 0.1 g and 5 g of catalyst per mole of 5-ketogluconic acid used.

Under the conditions described above, the oxidative alkaline degradation reaction usually goes to completion in about 3 to 24 hours.

This completion may conveniently be assessed by measuring the reductive power, with respect to a cupro-tartrosodic reagent for example, of the reaction medium.

The reaction is preferably stopped when the reaction medium shows only a reductive power of less than 5%, preferably of less than 2%, of the initial reductive power.

At this stage, such a crude reaction mixture may constitute, after any possible catalysts have been removed and preferably after drying, an excellent complexing base for washing products. The impurities present, which are essentially small amounts of gluconic, glyceric, tartronic, malic, tartaric, erythronic, etc. acids and larger amounts of formic acid, do indeed themselves also possess non-negligible complexing properties.

However, when it is desired to obtain xylaric acid at a purity which allows its use in the synthesis of polyhydroxy-polyamides or xylitol, it is preferable, when the alkaline oxidative degradation reaction has been carried out on 5-ketogluconic acid in the form of one of its very soluble salts, in particular the sodium or potassium salt, for the xylaric acid to be precipitated in the form of its calcium salt by adding lime, calcium chloride or calcium carbonate, for example, in stoichiometric amount or in slight excess to the reaction medium.

The reason for this is that the Applicant Company has observed that calcium xylarate is of extremely low solubility in water, in contrast with the calcium salts of the other acids which are very often present, even in low amounts after the alkaline oxidative degradation reaction, and in contrast with formic acid which is always present. The subject of the present invention is thus also a process for the manufacture of xylaric acid obtained by oxidative alkaline degradation of 5-ketogluconic acid, characterized in that it consists in manufacturing and in isolating calcium xylarate as intermediate product.

In order to obtain a calcium xylarate precipitate which can be filtered more easily, this operation may be carried out at an elevated temperature, which may be up to the boiling point of the reaction medium.

After cooling of the reaction medium, the precipitated calcium xylarate is isolated by simple filtration. The soluble calcium salts held by the filter cake may be removed by washing this cake. Such a washing operation allows removal of the impurities which are formed during the step of alkaline oxidative degradation of the 5-ketogluconate. It especially allows removal of the formate which is produced at the same time as the xylarate during this step.

The xylaric acid may then be released from its calcium salt using an acid such as oxalic acid or sulphuric acid. Here also, heating of the reaction medium to about 70° C. followed by cooling will make it possible to obtain crystals of calcium oxalate or sulphate which are better formed and easier to filter off.

It is also recommended, in this step of release of the xylaric acid, to use the sulphuric acid or the oxalic acid in an amount which is only slightly less than the stoichiometry, the calcium still present being removed later by demineralization on a cationic resin. This procedure prevents there being too much sulphuric or oxalic acid in the xylaric acid solution, which would be difficult to eliminate later.

By simply concentrating the xylaric acid solution obtained by the cationic resin to a solids content of greater than 50%, crystals of this acid may be obtained without the need for any organic solvent. It is preferred to carry out this concentrating operation at low temperature and thus in an apparatus operating under vacuum. Better formed and much more uniform crystals are obtained when the concentrated solution, which is slightly supersaturated with xylaric acid, is seeded with ground crystals of this acid. Similarly, it is preferable, after this evaporation, to cool the crystal broth obtained slowly and with gentle stirring so as to facilitate the subsequent fractionation thereof.

The crystals of xylaric acid, with a chemical purity of greater than 98%, are then readily isolated from the crystal broth obtained above simply by draining under the action of a centrifugal force. It may also be advantageous, when it is desired to increase the purity of the crystals further, to spray the cake of crystals undergoing draining with a little water, so as to remove virtually all of the mother liquors in which they were formed.

These mother liquors may be subjected to a further concentrating operation, which then gives a second crop of xylaric acid crystals. These liquors may also be recycled with the contents of the reactor immediately after the alkaline oxidative degradation reaction of the 5-ketogluconic acid.

The xylaric acid thus obtained may be used as a starting material in the manufacture of polyhydroxypolyamides.

It may also undergo, preferably after lactonization, a catalytic hydrogenation using a ruthenium catalyst, for example, in order to obtain xylitol.

The examples which follow are given in order to illustrate the invention and to allow a better understanding of it to be gained. They should not be considered as being limiting, in particular as regards the nature of the 5-ketogluconic acid salt used for the oxidative alkaline degradation reaction or that of the acids employed to release the 5-ketogluconic or xylaric acids.

EXAMPLES

Example 1

Alkaline Oxidative Degradation of 5-ketogluconic Acid

A suspension containing 10% calcium 5-ketogluconate is treated with a stoichiometric amount of oxalic acid, the suspension being maintained at 70° C. for one hour with stirring.

After cooling, the mixture is filtered through a prelayer of filtering earth in order to remove the calcium oxalate.

A clear, slightly orange-coloured solution of 5-ketogluconic acid is obtained, which is percolated through a strong cationic resin column in order to remove any possible excess calcium.

After neutralizing this 5-ketogluconic acid solution to pH 7.0 with washing soda, it is concentrated under vacuum to a solids content of 50%, corresponding to a density of 1.294 g/cm$^3$.

7 liters of water and 787.2 g of 50% washing soda, i.e. 9.84 mol of NaOH, are introduced into a glass fermenter tank with a useful volume of 15 liters, and this solution is brought to 40° C. and then aerated for 30 minutes.

12 grams of sodium anthraquinone 2-sulphonate, i.e. 3.7·10$^{-2}$ mol, and 4 cm$^3$ of aqueous 30% hydrogen peroxide solution, i.e. 4·10$^{-2}$ mol of H$_2$O$_2$, are then added to this solution. Next, 1374 cm$^3$ of the sodium 5-ketogluconate solution obtained above are added continuously to this reactor at an approximate flow rate of 8 ml/min for 170 minutes, i.e. a total of 4.1 mol of sodium 5-ketogluconate.

During this period, the stirring and aeration of the reaction medium are adjusted so as to maintain a pink colour in this medium. This colour indicates that there is neither an excess nor a deficit of dissolved oxygen in the fermenter which serves as the reactor.

After 170 minutes, with the aeration and stirring being maintained, the temperature is increased to 50° C., and after 255 minutes it is brought to 60° C. The reaction is stopped after 375 minutes.

The content of reducing sugars in the reaction medium, expressed as "glucose equivalent", as measured with cuprotartro-sodic liquor, then steadies at 1.15 g per liter of reaction medium, thereby indicating a reductive power equivalent to 10 g of reducing sugars present in the reaction medium, i.e. about 0.057 mol of "glucose equivalent", i.e. still about 1.4% of the initial reductive power: 0.057×100/4.1.

This reaction medium, which is dark red when all aeration is stopped, is then treated on a column of granular active charcoal, after the pH has been adjusted to 5.5 by addition of 25 ml of sulphuric acid of density 1.98, so as to remove the sodium anthraquinone 2-sulphonate therefrom, and is then concentrated to a solids content of 20.4%.

The analysis carried out on this product gave the following results:

xylaric acid: 77.8 g/l
formic acid: 27.7 g/l
glycolic acid: 11.6 g/l
glyceric acid: 1.7 g/l
tartaric acid: 11.9 g/l
malic acid: 4.4 g/l
tartronic acid: 7 g/l
disodium sulphate: 50 g/l After spray-drying, such a crude product, containing the sodium salts of xylaric and formic acids and also, in lesser amounts, those of glycolic, glyceric, tartaric, malic, tartronic, etc. acids, may form an excellent calcium-chelating base and its properties may be exploited in particular in washing formulations based on detergent compositions which are phosphate-free or have a reduced phosphate content.

At this stage, the molar yield of sodium xylarate reaches 51.4% relative to the 5-ketogluconate used. It may readily be improved by carrying out the alkaline oxidative degradation of the 5-ketogluconic acid using oxygen and/or by working under pressure.

Example 2

Purification of Xylaric Acid

The crude reaction medium, concentrated to 20.4%, obtained in Example 1 is treated with calcium carbonate at a rate of half a mole of calcium carbonate per mole of sodium present. This treatment is carried out with stirring at a temperature in the region of 100° C. After cooling, an abundant white precipitate consisting essentially of very sparingly soluble calcium xylarate is observed.

This precipitate is filtered off and washed with a little cold water and is then resuspended in water so as to obtain a milk with a solids content of about 20%. This milk is next brought to 70° C. and a sufficient amount of oxalic acid to precipitate about 95% of the calcium present in the form of calcium oxalate is then added thereto. This milk is then left to cool slowly with gentle stirring, followed by elimination of the oxalate by filtration, which gives a crude solution of xylaric acid from which the residual calcium is removed by percolation through a strong cationic resin.

This solution is then concentrated under vacuum to a solids content of 50%, followed by seeding with ground crystals of xylaric acid, after which the evaporation is continued until a thick mass of crystals is obtained.

Draining of these crystals after washing on a drainer, followed by drying in a fluidized bed apparatus with air at 50° C., gives very pretty crystals of xylaric acid in a purity of 99.2%.

Example 3

Use of Xylaric Acid for the Synthesis of Xylitol

Xylaric acid crystals were melted in air for 30 minutes at a temperature of 145° C.

The liquid obtained set to a solid lump on cooling and this lump was ground to give a white powder corresponding to the following analysis:

| | |
|---|---|
| xylaric acid | 11% |
| lactone | 78% |
| dimers | 11% |

This powder was redissolved in water, to a solids content of 40%, and this solution was then placed under a hydrogen pressure of 80 bar, at 130° C. in the presence of a catalyst consisting of 2% ruthenium supported on active charcoal, at a rate of 0.2% ruthenium relative to the solids content used.

Analysis of the product resulting from this hydrogenation showed the presence of 3.7% xylitol after reaction for 5 hours.

Example 4

Use of Xylaric Acid as a Calcium-chelating Agent

The sequestering power of the xylarate obtained in Example 1 was measured at pH 10 and at a temperature of 40° C. in the presence of boric acid, and was compared with the sequestering power of sodium citrate and sodium tripolyphosphate.

The results are expressed in milligrams of chelated calcium per gram of dry product xylarate: 58 citrate: 68 tripolyphosphate: 155

It is thus observed that the crude product of Example 1, which is rich in xylarate, can claim, on account of its good sequestering power, to be of use in washing compositions.

I claim:

1. Process for the manufacture of xylaric acid, consisting in oxidatively degrading 5-ketogluconic acid or a salt of 5-ketogluconic acid with oxygen or a gas containing it as a reactant in an alkaline medium, and subsequently recovering the xylatic acid thus formed.

2. Process according to claim 1, wherein the alkaline medium is provided by the addition of a basic salt of 5-ketogluconic acid.

3. Process according to claim 1, wherein the 5-ketogluconic acid or a salt of 5-ketogluconic acid is oxidatively degraded at a pH of above 12.5.

4. Process according to claim 1, wherein the reactant is finely divided in the medium.

5. Process according to claim 1, wherein the alkaline medium is provided by the addition of a base.

6. Process according to claim 1, wherein the oxidative degradation is carried out in the presence of catalysts.

7. Process according the claim 1, wherein the oxidative degradation is carried out under pressure.

8. Process according to claim 6, wherein the catalyst is an equimolar mixture of anthraquinone 2-sulphonate and hydrogen peroxide.

9. Process according to claim 1, wherein the oxidative degradation is carried out at a temperature ranging between 20° and 60° C.

10. Process according to claim 1, wherein the oxidative degradation is carried out during about 3 to 24 hours.

11. Process according to claim 1, wherein the oxidative degradation is carried out until the reaction medium shows a reductive power of less than 5% of the initial reductive power.

12. Process according to claim 11, wherein the oxidative degradation is carried out until the reaction medium shows a reductive power of less than 2% of the initial reductive power.

13. Process according to claim 1, wherein xylaric acid is recovered from the reaction medium by adding thereto lime, calcium chloride, or calcium carbonate in stiochiometric amounts or in slight excess with respect to the amount of xylaric acid formed, recovering the precipitated calcium xylarate thus formed and treating it with an acid selected from the group consisting of oxalic acid and sulfuric acid.

14. Process according to claim 13, wherein the calcium xylarate is isolated by filtration.

* * * * *